United States Patent [19]
Nakano et al.

[11] 3,995,632
[45] * Dec. 7, 1976

[54] OSMOTIC DISPENSER

[75] Inventors: Masahiro Nakano; Takeru Higuchi; Anwar Hussain, all of Lawrence, Kans.

[73] Assignee: Alza Corporation, Palo Alto, Calif.

[ * ] Notice: The portion of the term of this patent subsequent to Dec. 30, 1992, has been disclaimed.

[22] Filed: Sept. 30, 1974

[21] Appl. No.: 510,753

Related U.S. Application Data

[63] Continuation of Ser. No. 357,228, May 4, 1973, abandoned, which is a continuation of Ser. No. 106,133, Jan. 13, 1971, abandoned.

[52] U.S. Cl. .............................. 128/260; 128/172; 128/271; 222/95
[51] Int. Cl.² .......................................... A61M 31/00
[58] Field of Search ........................ 128/128–131, 128/172, 213, 252, 260, 271, 272, 193, 261; 222/386.5, 386, 389, 94, 95, 97, 105, 106, 130; 210/23

[56] References Cited

UNITED STATES PATENTS

| | | | |
|---|---|---|---|
| 1,175,129 | 3/1916 | Crittenden | 128/261 |
| 2,928,769 | 3/1960 | Gaunt | 128/271 X |
| 2,962,023 | 11/1960 | Chappaz et al. | 128/271 |
| 3,087,860 | 4/1963 | Endicott | 128/271 |
| 3,136,695 | 6/1964 | Tansey | 424/22 |
| 3,415,249 | 12/1968 | Sperti | 128/271 |
| 3,424,158 | 1/1969 | Silver | 128/271 X |
| 3,577,512 | 5/1971 | Shepherd et al. | 424/22 |
| 3,604,417 | 9/1971 | Stolzenberg | 128/213 |
| 3,608,549 | 9/1971 | Merrill | 128/260 |

Primary Examiner—Aldrich F. Medbery
Attorney, Agent, or Firm—Bacon & Thomas

[57] ABSTRACT

An osmotic dispenser is described which is capable of releasing to its outside environment concentrations of active agent at an osmotically controlled rate over a prolonged period of time, and the active agent formulation of which is a solid or semisolid at storage temperatures, advantageously room temperature, and is fluid at the temperature of the prospective situs for the osmotic dispenser, typically at body temperature.

12 Claims, 1 Drawing Figure

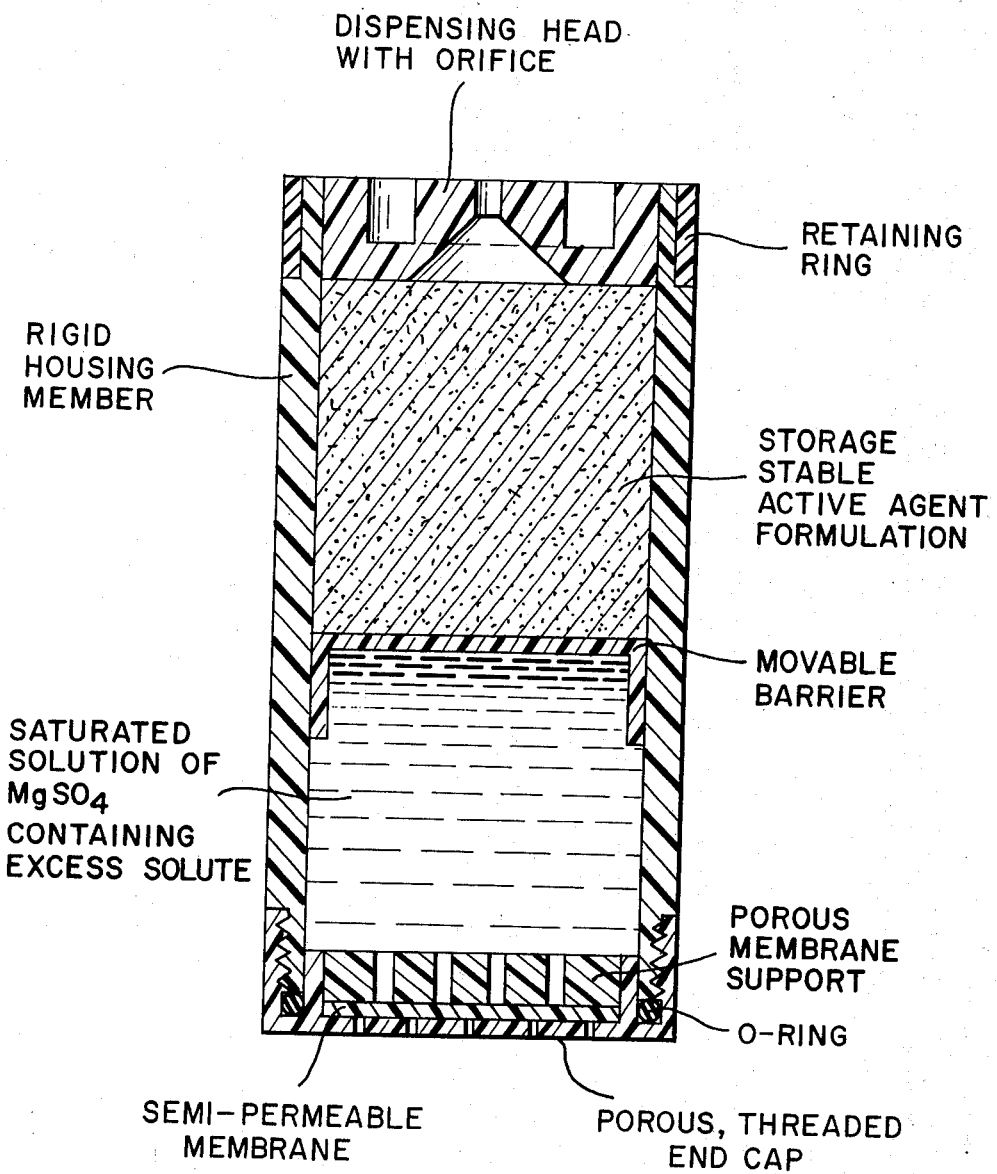

OSMOTIC DISPENSER

This is a continuation of application Ser. No. 357,228, filed May 4, 1973, which is a continuation of Ser. No. 106,133 filed Jan. 13, 1971 each abandoned.

CROSS REFERENCE TO RELATED APPLICATIONS

Takeru Higuchi copending application, Ser. No. 106,131, filed Jan. 13, 1971, now U.S. Pat. No. 3,760,805, assigned to the assignee of the present invention;

Takeru Higuchi and Harold H. Leeper copending application, Ser. No. 106,130, filed Jan. 13, 1971, now U.S. Pat. No. 3,732,865, also assigned to the assignee of the present invention;

Harold M. Leeper copending application, Ser. No. 106,132 filed Jan. 13, 1971, now U.S. Pat. No. 3,760,806, also assigned to the assignee of the present invention; and Takeru Higuchi and Harold M. Leeper copending application, Ser. No. 106,161, filed Jan. 13, 1971, also assigned to the assignee of the present invention.

PRIOR ART

Rose and Nelson, *Austral. J. exp. Biol.*, 33 pp. 415 – 420 (1955); Rose and Nelson, *Austral. J. exp. Biol.*, 33 pp. 411–414 (1955).

FIELD OF THE INVENTION

This invention relates to an osmotic dispenser, and more especially, to an osmotic dispenser, simple in construction, capable of releasing to its outside environment concentrations of active agent at an osmotically controlled rate over a prolonged period of time.

DEFINITION OF TERMS

The expression "active agent" as used herein denotes any drug (as defined, infra); composition in any way affecting any biological entity; substance having a nutrient or stimulating action, or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable active agents for use with the dispenser of this invention include, without limitation, those which are generally capable of:

1. Preventing, alleviating, treating or curing abnormal and pathological conditions of the living body by such means as destroying a parasitic organism or limiting the effect of the disease or abnormality by chemically altering the physiology of the host or parasite;
2. Maintaining, increasing, decreasing, limiting or destroying a physiologic body or plant function, e.g., vitamin compositions, sex sterilants, fertility inhibitors, fertility promoters, growth promoters, and the like;
3. Diagnosing a physiological condition or state;
4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides, and the like;
5. Preserving, disinfecting or sterilizing; and
6. Controlling or affecting generically an environment, as by introducing a catalyst or metering a reactant into a reacting chemical system, or by effecting any chemical process therein, such as a fermentation, including propagation and/or attenuation of a microorganism.

The terms "environment", "surroundings " and "habitat" as used hereinabove and herein denote any prospective situs for the osmotic dispenser of this invention, or at least for the water permeable membrane component thereof, which is comprised of or will provide sufficient water for absorption into the device to develop the needed osmotic pressure on which its motive force depends; and implicit in the foregoing definition of "active agent" - one that will develop its action in the presence of such environment, surroundings or habitat, or one that will develop its action in a remote and/or another environment, which need not be aqueous.

Any of the drugs used to treat the body, both topical and systemic, can be compartmentalized as the active agent in any of the osmotic dispensers of this invention. "Drug" is used herein in its broadest sense as including any composition of substance that will produce a pharmacological or biological response.

Suitable drugs for use in therapy with the dispenser of the invention include without limitation:

1. Protein drugs such as insulin;
2. Desensitizing agents such as ragweed pollen antigens, hay fever pollen antigens, dust antigen and milk antigen;
3. Vaccines such as small pox, yellow fever, distemper, hog cholera, fowl pox, antivenom, scarlet fever, diphtheria toxoid, tetanus toxoid, pigeon pox, whooping cough, influenzae, rabies, mumps, measles, poliomyelitis, Newcastle disease, etc.;
4. Anti-infectives, such as antibiotics, including penicillin, tetracycline, chlortetracycline, bacitracin, nystatin, streptomycin, neomycin, polymyxin, gramicidin, oxytetracycline, chloramphenicol, and erythromycin; sulfonamide, including sulfacetamide, sulfamethizole, sulfamethazine, sulfadiazine, sulfamerazine, and sulfisoxazole; anti-virals including idoxuridine; and other anti-infectives including nitrofurazone and sodium propionate;
5. Anti-allergenics such as antazoline, methapyrilene, chlorpheniramine, pyrilamine and prophenpyridamine;
6. Anti-inflammatories such as hydrocortisone; cortisone, hydrocortisone acetate, dexamethasone, dexamethasone, 21-phosphate, fluocinolone, triamcinolone, medrysone, prednisolone, prednisolone 21-phosphate, and prednisolone acetate;
7. Decongestants such as phenylephrine, naphazoline, and tetrahydrozoline;
8. Miotics and anticholinesterases such as pilocarpine, eserine salicylate, carbachol, di-isopropyl fluorophosphate, phospholine iodide, and demecarium bromide;
9. Mydriatics such as atropine sulfate, cyclopentolate, homatropine, scopolamine, tropicamide, eucatropine, and hydroxyamphetamine;
10. Sympathomimetics such as epinephrine;
11. Sedatives and Hypnotics such as pentobarbital sodium, phenobarbital, secobarbital sodium, codeine, (α-bromoisovaleryl) urea, carbromal;
12. Psychic Energizers such as 3-(2-aminopropyl) indole acetate and 3-(2-aminobutyl) indole acetate;

13. Tranquilizers such as reserpine, chlorpromazine, and thiopropazate;

14. Androgenic steroids such as methyltestosterone and fluoxymesterone;

15. Estrogens such as estrone, 17 β-estradiol, ethinyl estradiol, and diethyl stilbesterol;

16. Progestational agents such as progesterone, negestrol, melengestrol, chlormadinone, ethisterone, norethynodrel, 19-nor-progesterone, norethindrone, medroxyprogesterone and 17α-hydroxy-progesterone;

17. Humoral agents such as the prostaglandins, for example, $PGE_1$, $PGE_2$, and $PGF_2$;

18. Antipyretics such as aspirin, sodium salicylate, and salicylamide;

19. Antispasmodics such as atropine, methantheline, papaverine, and methscopolamine bromide;

20. Anti-malarials such as the 4-aminoquinolines, 8-aminoquinolines, chloroquine, and pyrimethamine;

21. Antihistamines such as diphenhydramine, dimenhydrinate; tripelennamine, perphenazine, and carphenazine;

22. Cardioactive agents such as hydrochlorothiazide, flumethiazide, chlorothiazide, and trolnitrate;

23. Nutritional agents such as vitamins, essential amino acids and essential fats;

24. Anti-Parkinsonism agents such as L-dopa, (L-3,4-dihydroxyphenylalanine);

25. Investigative antihypotensive agents such as dopamine, 4-(2-aminoethyl) pyrocatechol.

Other drugs having the same or different physiological activity as those recited above can be employed in osmotic dispensers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts such as hydrochloride, hydrobromide, sulphate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amide, etc.) which have desirable retention and release characteristics but which are easily hydrolyzed by body pH, emzymes, etc., can be employed.

The amount of drug incorporated in the osmotic dispenser varies widely depending on the particular drug, the desired therapeutic effect, and the time span for which it takes the drug to be released. Since a variety of dispensers in a variety of sizes and shapes are intended to provide complete dosage regimes for therapy for a variety of maladies, there is not critical upper limit on the amount of drug incorporated in the dispenser. The lower limit too will depend on the activity of the drug and the time span of its release from the dispenser. Thus it is not practical to define a range for the therapeutically effective amount of drug to be released by the dispenser.

BACKGROUND OF THE INVENTION

Osmotic dispensers have heretofore been proposed, each of which is capable of dispensing concentrations of active agent at an osmotically controlled rate over a prolonged period of time.

Typically, these osmotic dispensers are comprised of a first compartment of relatively impervious material containing an active agent and a second compartment or chamber of controlled permeability to water containing a solution of an osmotically effective solute which exhibits an osmotic pressure gradient against water. Such devices are so constructed that, when placed in or functionally exposed to* a hypotonic aqueous environment, water is absorbed therefrom by osmosis and diffuses into the solution contained in the second compartment. As the water flows into the second compartment, the solution contained therein and in certain instances the compartment itself increase in volume, thus generating, either directly or indirectly, mechanical pressure or force on the active agent containing first compartment. The said first compartment is provided with any suitable dispensing head for releasing its active agent content to the exterior of the dispenser and individually is of a construction that its active volume is inversely responsive to the pressure thus exerted, i.e., is of such construction that, in use, the volume of same diminishes in a direct proportion to and as a consequence of increase in volume in the said second compartment. Hence, the rate and amount of release of the active agent are directly proportional to the change in volume in the second compartment, but inversely proportional to the volume change in the first. That is, as the water flows into the device, the second compartment increases in volume generating corresponding pressure or force on the first, either directly or indirectly, as by transmitting pressure against a separate or common wall member thereof, which wall member is yielding to such pressure, or by biasing a movable barrier into or against the first compartment or a wall member defining the same. The volume of said first compartment is thus constantly diminished and active agent is correspondingly continuously squeezed thereout at an osmotically controlled rate over a prolonged period of time.

*By "functionally exposed to" it is intended that, for example, such devices may be provided with their own self-contained water supply or separate water compartment, as in the first mentioned Rose and Nelson publication, supra.

In the aforementioned related applications, the disclosures of which are hereby incorporated by reference and are relied upon, there are described and claimed several osmotic active agent dispensers of the immediately above type.

For example, in Higuchi copending application, Ser. No. 106,131 filed Jan. 13, 1971, now U.S. Pat. No. 3,760,805, an osmotic dispenser is comprised of a water permeable housing member, advantageously rigid, confining a first flexible bag of relatively impervious material containing the active agent, advantageously a drug, preferably in a gel, paste or other semisolid state (albeit a solution or a concentrated solution of active agent will sometimes suffice), and a second bag of controlled permeability to moisture containing a solution of an osmotically effective solute which exhibits an osmotic pressure gradient against water. The said first and second bags are disposed within the said water permeable housing member or porous shell such that water permeates from the environment through the porous shell or housing and migrates by osmosis into the solution contained in the second bag. The solution in the second bag increases in volume, exerting mechanical force on the active agent containing first bag, which mechanical force in turn ejects the active agent out of the apparatus. For purposes of permitting the active agent to be squeezed out of the said first flexible bag, same is provided with any suitable active agent release means or dispensing head to the exterior of the device, e.g., long plastic tubing extending through the porous shell, or ductlike fine tubule connections therethrough.

Higuchi and Leeper copending application, Ser. No. 106,130, filed Jan. 13, 1971, now U.S. Pat. No. 3,732,865, relates to an osmotic dispenser comprised of a first compartment of relatively impervious material containing an active agent and a second compartment containing a solution of an osmotically effective solute which exhibits an osmotic pressure gradient against water Separating the said first from the said second compartment, and defining a wall member common to each of said compartments, is a sliding or movable barrier of impervious material. The enclosure, whether of integral construction or not, defining the remainder of the second compartment, wherein the osmotic motive force of the dispenser is developed, is at least in part comprised of membrane which exhibits controlled permeability to water. When placed in a hypotonic aqueous environmet, water, by osmosis, is absorbed therefrom through the membrane and diffuses into the solution contained in the said second compartment. As the water flows into the second compartment, the solution contained therein increases in volume exerting corresponding pressure behind the movable barrier divider. Such pressure serves to drive the said barrier forward and into the active agent compartment thus diminishing the volume of same, and which sliding barrier in turn ejects the active agent out of the apparatus at an osmotically controlled rate over a prolonged period of time. For purposes of permitting the active agent to be squeezed out of the first compartment, same also is provided with any suitable dispensing head or active agent release means to the exterior of the device, for example, capillary ducts therethrough. A further feature of this invention resides in an osmotic active agent dispenser comprised of a plurality of capsule half shells, similar in shape to pharmaceutical hard gelatin half shells, with a first and a second half shell being securely affixed in capsular configuration, and a third half shell frictionally disposed in such capsule but free to slidably move therein. The said capsule is thereby divided into the two compartments with the third half shell defining the wall member common to each of same.

And Leeper copending application, Ser. No. 106,132, filed Jan. 13, 1971, now U.S. Pat. No. 3,760,806, describes an osmotic dispenser comprised of a first helical compartment of relatively impervious material containing an active agent and a second helical compartment containing a solution of an osmotically effective solute which exhibits an osmotic pressure gradient against water. The two helical compartments are interconnected so as to define a continuous helix. Separating the first helical compartment from the second helical compartment, and defining a wall member common to each of said compartments, is a sliding or movable barrier of impervious material capable of traversing the helix, advantageously a plastic or glass ball separator. The enclosure, whether of integral construction or not, defining the remainder of the second compartment wherein the osmotic motive force of the dispenser is developed, is at least in part comprised of membrane material which exhibits controlled permeability to water. When placed in a hypotonic aqueous environment, water, by osmosis, is absorbed therefrom through the membrane and diffuses into the solution contained in the second compartment. As the water flows into the second compartment, the solution contained therein increases in volume exerting corresponding pressure behind the movable barrier divider. Such pressure serves to drive the said barrier forward and into the active agent compartment thus diminishing the volume of the same, and which sliding or rolling barrier in turn ejects the active agent out of the apparatus at an osmotically controlled rate over a prolonged period of time. For the purpose of permitting the active agent to be squeezed out of the first compartment, the same is provided at its terminal point with any suitable dispensing head or active agent release means to the exterior of the device, for example, a capillary duct therethrough. A further feature of this invention resides in an osmotic active agent dispenser comprised of a dispenser according to the foregoing description enveloped by a relatively rigid, highly permeable housing member. The housing member serves both as a protective means for the dispenser and also to restrict expansion of the dispenser due to internal pressure. Alternatively, such expansion may be in and of itself restricted by means of any suitable bond or tie member.

The osmotic active agent dispenser described in Higuchi and Leeper copending application, Ser. No. 106,161, filed Jan. 13, 1971, is comprised of a chamber having controlled permeability to water and containing a solution of an osmotically effective solute which exhibits an osmotic pressure gradient against water, said chamber housing a flexible bag of relatively impervious material containing an active agent and provided with means or dispensing head for releasing said active agent to the exterior of the dispenser. The flexible bag is disposed within the said housing chamber such that as water permeates from the external environment through the permeable walls of the chamber and migrates or diffuses by osmosis into the solution contained therein, same increases in volume thereby generating mechanical compressing or deflating force on the flexible bag, which force in turn ejects the active agent out of the apparatus at an osmotically controlled rate over a prolonged period of time.

The osmotic dispenser proposed in the Rose and Nelson article, supra, too is capable of delivering drug solution at a relatively constant rate. This injector consists of three compartments and a clamp to hold a semi-permeable membrane. The motive force of the injector depends on the osmotic pressure developed by a saturated aqueous solution of Congo red against water. This solution is contained in a partially collapsed rubber compartment and is separated from a second water compartment by the semi-permeable cellophane membrane. The partially collapsed bag is placed in a glass ampoule, with the drug compartment of the device being defined by the space between the Congo red bag and the glass ampoule. The ampoule is also provided with drug release means and when the drug compartment is charged with a drug solution water will move by osmosis into the Congo red solution, thus expanding the rubber compartment and providing the mechanical force to eject the drug out of the apparatus.

The compartment or chamber of the aforesaid osmotic active agent dispensers containing the solution of the osmotically effective solute, wherein the osmotic motive force of the respective devices is developed, is at least in part comprised of membrane which exhibits controlled permeability to water. Such membrane can be formed from a wide variety of materials permeable or semi-permeable to solvent (water) but not to solute, i.e., those suitable for the construction of an osmotic cell. Typical membranes are isotropic membranes such as unplasticized cellulose acetate, plasticized cellulose acetate, reinforced cellulose acetate, cellulose di- and triacetate, ethyl cellulose; anisotropic reverse osmosis membranes which typically are made of cellulose acetate; silicone rubbers, polyurethanes, natural rubber, and hydrolyzed ethylene/vinyl acetate copolymers. Isotropic membranes have less water permeability than do the anisotropic membranes. Also, with both types of membranes, increasing the acetate content of the cellulose acetate polymer decreases the water permeability. In devices, the surface areas of the membranes of which are relatively limited, it will be preferred to use semi-permeable membranes allowing relatively rapid water transmission. Thus, in such embodiments the anisotropic membranes are the preferred. For drug depot applications as heretofore described, the membranes are also biologically inert, non-irritating to body tissues and non-allergenic. So too in such applications are the other materials from which the topic dispensers are fabricated. For best results, the membrane should be substantially impermeable to passage of the osmotically effective solute so as to prevent loss thereof.

In the osmotic dispenser proposed by Rose and Nelson, supra, the active agent is employed in the form of a solution. Consequently, there result several disadvantages as regards the handling of such osmotic devices, e.g., spillage and loss of active ingredient, as well as in their storage capabilities since drug containing solutions generally have a relatively short shelf life, and many chemical substances on prolonged storage in a dissolved state undergo chemical deterioration. Furthermore, the use of solutions in osmotic devices places an absolute upper limit on the concentration of active agent that can be administered from a given volume of composition. This latter limitation is of great importance when overall size limitations of such devices are considered. Moreover, drug or other active agent solutions exhibit the deleterious tendency to be released from an osmotic device by simple leaching.

SUMMARY OF THE INVENTION

Accordingly, it is a primary object of this invention to provide an osmotic dispenser, simple in construction, which exhibits all of the practical benefits of long term continuous administration of various active agents both to animals, humans and into other environments.

Another object of this invention is to provide an improved osmotic dispenser which overcomes handling and storage problems inherent in related devices heretofore proposed.

Another object of the invention resides in the provision of an improved osmotic dispenser which enables high concentrations of active agent to be administered therefrom, and which high concentrations of active agent will not exhibit the tendency to be leached from the device, nor be decreased in potency by chemical breakdown.

In attaining the objects of this invention, one feature resides in an osmotic active agent dispenser, the active agent formulation of which is a solid or semisolid at storage temperature, advantageously at room temperature, and is fluid at the temperature of the prospective situs for the osmotic dispenser, typically body temperature. In a preferred embodiment, the active agent formulation comprises the active agent dispersed or dissolved in an inert carrier. Optionally, there may be included together with the active agent and carrier one or more additional ingredients, such as a surfactant, an anti-oxidant, and/or a dispersed inert particulate solid filler.

Other objects, features and advantages of this invention will become more apparent from the following description.

DETAILED DESCRIPTION OF THE INVENTION

In accordance with this invention, it has been discovered that significant advantages may be obtained by employing in the subject osmotic dispensers an active agent formulation which is a solid or semisolid at storage temperature and fluid at the temperature of the prospective situs for the osmotic dispenser. By employing such a formulation, dispensers of the invention exhibit superior handling convenience because there is no possibility for spillage or loss of active ingredient from the device, thereby assuring uniformity of dosage after fabrication of the device. Moreover, solid formulations are characterized by absence of chemical breakdown, and by storage stability which is greatly improved as compared with liquid active agent containing solutions which typically have a relatively short shelf life. In another aspect, a higher concentration of active agent can be administered from the same volume of composition as compared with the use of solutions, and there is no tendency for the solid formulations to be leached from the topic devices. Thus, the devices of this invention are capable of administering a wide range of active agent dosages while at the same time conforming to inherent overall size limitations.

Active agent formulations which are solid or semi-solid at storage temperature and fluid at the temperature of the prospective situs for the device may consist of active agent compounds or compositions per se exhibiting such properties, or more typically, may comprise an active agent in combination with a carrier exhibiting the foregoing properties. The selection of an active agent or carrier to achieve the desired result of course depends primarily upon the temperature of the environment in which the device is destined for ultimate application, since storage temperature is often a matter of choice. Preferably, devices according to the present invention are designed for storage at room temperature with ultimate deployment of the same in an environment having a temperature greater than room temperature. It will of course be appreciated that active agent formulations advantageously having storage temperatures below room temperature, e.g., under refrigeration, as well as those having storage temperatures above room temperature are contemplated within the scope of the present invention. One particularly advantageous application of the present osmotic dispenser lies in the area of administering drugs to human beings and other mammals, such as cattle. In such applications the temperature of the prospective situs for the dispenser is of course body temperature.

Typically, the active agent is employed in the form of a drug dispersed or dissolved in an inert carrier when use of the device as a drug depot is contemplated. A multitude of biologically inert, non-irritating to body tissues and nonallergenic suitable carrier materials are known, including those exemplified in the following table:

TABLE I

| Carrier | Composition | Melting Point ° C. |
|---|---|---|
| Cocoa butter | Triglycerides of oleic, palmitic and Stearic acids | 30 – 35 |
| Cotomar[a] | Partially hydrogenated cottonseed oil | 35 – 39 |
| Hard Butter S-70-XX[b] | Triglycerides | 36.5 |
| Suppositol H, S, T & R[c] | Hydrogenated coconut oil triglyceride | 34 – 38.5 |
| Wecobee W, R, S, M & FS[d] | Triglycerides derived from coconut and palm kernel oils | 31.7 – 40.5 |
| Witepsol H, W, S & E[e] | Triglycerides of $C_{12}$–$C_{18}$ fatty acids | 32 – 44 |
| Polyethylene glycols 600, 1000, 1540, 4000 and 6000[f] | Linear Polymers of ethylene oxide | 38 – 49 |
| Polymeg 1000 & 2000[g] | Polytetramethylene ether glycol | 38 |
| Myrj 52[h] | Polyoxyl 40 Stearate USP | 38 – 43 |
| Tween 61[h] | Polyethylene-4-Sorbitan monostearate | 35 – 39 |
| MYRJ 53[h] | Polyoxyethylene 50 stearate | 36 |
| BRIJ 58[h] | Polyoxyethylene 20 cetyl ether | 38 |
| BRIJ 76[h] | Polyoxyethylene 10 stearyl ether | 38 |
| BRIJ 78[h] | Polyoxyethylene 20 stearyl ether | 38 |

[a]Procter & Gamble
[b]Best Foods
[c]Fritz Wetz (four types vary in melting range with H the lowest and R the highest melting products)
[d]Drew (different types vary in melting range and in narrowness of the melting range)
[e]Dynamit Nobel (different types vary in melting range, but all have a narrow melting range)
[f]Union Carbide (blends of various polymers are used to formulate suppository bases)
[g]Quaker Oats
[h]Atlas The amount of active agent incorporated in the carrier varies widely depending on the particular active agent, the particular carrier and the desired dosage to be administered by the dispenser. Thus, there is no lower limit on the amount of active agent to be combined with the carrier, and likewise, there is no upper limit save for the physical limitation upon the carrier to contain a particular active agent and concurrently maintain the desired property of being a solid at storage temperatures. Thus, it is not practical to define a range for the amount of active agent to be incorporated in the inert carrier; however, in a typical active agent formulation, the carrier contains from 5 to 80 percent by weight of active agent, preferably from 35 to 75 percent.

When the drug or other active agent is insoluble in the carrier, a surfactant is advantageously included in the active agent formulation to enhance the physical stability of the suspension. The surfactant must be inert to the active agent as well as biologically inert, and accordingly non-ionic surfactants are preferred. Exemplary non-ionic surfactants include sorbitan monostearate, polysorbate 80 USP [polyoxyethylene (20) sorbitan monooleate], and polyoxyethylene 4 stearate. Several active agent-surfactant combinations have been found to be particularly effective, for example, sorbitan mono-stearate has been found effective to stabilize suspensions of tetracycline, while polyoxyethylene sorbitan monooleate has likewise been found suitable for use with chloramphenicol. A preferred range for the surfactant is typically between about 0.1 and 1 percent by weight of the total mix.

Optionally, the active agent formulations of the invention may include an anti-oxidant to prevent degradation during the prolonged periods of storage now made possible, usually in an amount of from about 0.01 to about 2% by weight of the active agent. Any of the food-approved anti-oxidants may be employed in this capacity, with the following being merely illustrative in this regard: tertiary butyl-4-methoxyphenol (mixture of 2- and 3- isomers), 2,6-ditertiary butyl-p-cresol, propyl gallate, 6-ethoxy-1,2-dihydro-2,2,4-trimethylquinoline (ethoxyquin) and nordihydroguaiaretic acid (NDGA).

Similarly, there is contemplated the optional inclusion of a dispersed inert particulate solid to the active agent formulations of the invention. These particulate solids are included typically in amounts of from 0.5 to 5% by weight of the active agent, to enhance the stability of the product by providing a high solids content. Thus, when low concentrations of drug or other active agent are employed or the drug is soluble in the carrier, an inert solid such as fumed silica, bentonite, etc., may be added to prevent the formulation from setting (settling) out should the device be inadvertently exposed to high temperatures.

While the foregoing description has been directed primarily to active agent formulations which are solid at room temperature and fluid at body temperature, it will be readily apparent that the basic principles involved apply equally to those applications of the present osmotic dispenser wherein the same are ultimately placed in other environments to dispense a given active ingredient formulation. Thus, for example, when the instant dispensers are employed in a polymerization reaction to dispense polymerization catalysts into the reaction vessel at a controlled rate over a prolonged period of time, the active agent formulation may comprise the polymerization catalyst dispersed in polymeric material identical to that being polymerized in the vessel, this formulation of course being solid at room temperature and typically fluid at the polymerization reaction temperature.

To further illustrate the present invention and the advantages thereof, the following specific examples are given, it being understood that the same are intended merely as illustrative and in no wise limitative:

EXAMPLE 1

1200 milligrams of tetracycline hydrochloride and 800 milligrams of polyethylene glycol 600 - polyethylene glycol 1000 mixture (6:4) containing 8 milligrams of sorbitan monostearate and 0.16 milligrams of 2,6-ditertiary butyl-p-cresol are mixed at 39° C. whereat the glycol mixture is a clear viscous liquid. Thereafter, the mixture is milled twice in an Asra mill, reheated and poured into the active agent compartment of an osmotic dispenser constructed in accordance with FIG.

4 of Higuchi and Leeper application, Ser. No. 106,130 filed Jan. 13, 1971, now U.S. Pat. No. 3,732,865. The active agent formulation is then allowed to cool to room temperature whereupon it solidifies to a storage-stable state. The osmotic dispenser is then placed in an aqueous solution at approximately 38° C., and the active agent formulation again melts to a liquid form and is forced out of the device through the dispensing head by the osmotic pressure developd in the osmotically effective solute compartment as a result of water from the environment permeating by osmosis thereinto. In FIG. 1 there is illustrated the device of this Example.

EXAMPLE 2

6000 milligrams of chloramphenical, 5000 milligrams of cocoa butter and 44 milligrams of Tween 80 (polyoxyethylene 20 sorbitan monooleate USP) are mixed at 39° C., milled twice in the Asra mill, reheated and poured into the active agent compartment of an osmotic device constructed in accordance with the design illustrated in FIG. 1 of Higuchi application, Ser. No. 106,131, filed Jan. 13, 1971, now U.S. Pat. No. 3,760,805. The active agent formulation is again a solid at room temperature, and is readily dispensed through the dispensing head of the device in response to an osmotic pressure developed therein when the device is placed in an aqueous environment at approximately 38° C.

EXAMPLE 3

An active agent formulation containing 13,000 milligrams tetracycline base (vacuum dried), 13,000 milligrams of cocoa butter and 104 milligrams of Span 60 (sorbitan monostearate USP) is prepared according to the procedure of Example 2 and poured into the active agent compartment of an osmotic dispenser constructed in accordance with FIG. 1 of Higuchi and Leeper application, Ser. No. 106,130 filed Jan. 13, 1971, now U.S. Pat. No. 3,732,865. The resulting formulation is again solid at room temperature, storage stable thereat and again an easily dispensible liquid at approximately 38° C.

EXAMPLE 4

An active agent formulation containing 1000 milligrams of cocoa butter, 1200 milligrams of sulfisoxazole, 8.8 milligrams of Span 60 (sorbitan monostearate), and 0.2 milligrams of 2,6-ditertiary-butyl-p-cresol is prepared according to the procedure of Example 2, and poured into the active agent compartment of a device identical to that employed in Example 2. Results essentially identical to the foregoing examples are obtained.

The osmotic dispenser can be fabricated in any convenient shape for either physical insertion or implantation in the body, or for administration via the gastrointestinal tract, or for introduction into any desired environment. Dimensions of the device can thus vary widely and are not of controlling importance. The lower limit of the size of the device is governed by the amount of the particular active agent to be supplied to the environment to elicit the desired response, as well as by the form the dosage unit takes, for example, in cases of specific body uses, implantate, bolus, IUD, IVD, vaginal ring, uterine capsule for fertility suppression, artificial gland, pessary, prosthesis, suppository, and the like.

Thus, the invention provides, in an osmotic dispenser, a reliable means for releasing effective concentrations of active agent contained therein to the body of a living organism, or to any other environment, at an osmotically controlled rate and over a prolonged period of time. In addition, by providing an active agent formulation which is solid or semisolid at storage temperatures and fluid at the temperature of the prospective situs of the dispenser, the active agent formulation will not be decreased in potency by chemical breakdown and exhibits enhanced storage stability and handling characteristics as well as advantageous high concentrations of the active ingredient itself, and same will not exhibit the tendency to be leached from the device.

While the invention has been described and illustrated with reference to certain preferred embodiments thereof, those skilled in the art will appreciate that various modifications, changes, omissions, and substitutions can be made without departing from the spirit of the invention. It is intended therefore, that the invention be limited only by the scope of the following claims.

What is claimed is:

1. An osmotic active agent dispenser comprised of a first compartment of relatively impervious material containing an active agent and provided with means for releasing the active agent to the exterior of the dispenser, and a second compartment of controlled permeability to water containing a solution of an osmotically effective solute which exhibits an osmotic pressure gradient against water, the said first and second compartments having a barrier member such that the said first compartment diminishes in volume in response to an increase in volume of the solution in the said second compartment via absorption of water by osmosis therein, and defining a means for establishing a substantially zero order rate of release, as water flows into the dispenser in a tendency towards osmotic equilibrium with its environment, so that the active agent is continuously squeezed thereout at an osmotically controlled rate over a prolonged period of time; said active agent formulated in a form which is a chemically stable solid or semisolid at storage temperatures but a readily dispensible melt at the temperatures of the prospective situs for the osmotic dispenser, whereby the stability and uniformity of dosage of the said active agent over the said prolonged period of time are assured.

2. The osmotic dispenser as defined by claim 1, wherein the active agent formulation comprises the active agent in combination with a carrier.

3. The osmotic dispenser as defined by claim 2, wherein the active agent carrier is a solid at room temperature.

4. The osmotic dispenser as defined by claim 3, wherein the active agent carrier is a melt at body temperature.

5. The osmotic dispenser as defined by claim 4, wherein the active agent carrier is a member selected from the group consisting of glycerides; polytetramethylene ether glycols, methyl cinnamate; polyoxyethylene glycol; polyoxyethylene 4 sorbitan monostearate; polyoxyethylene fatty acid esters selected from the group consisting of polyoxyethylene 40 stearate and polyoxyethylene 50 stearate; and polyoxyethylene fatty alcohol ethers selected from the group consisting of polyoxyethylene 10 stearyl ether polyoxyethylene 20 stearyl ether and polyoxyethylene 20 cetyl ether.

6. The osmotic dispenser as defined by claim 1, wherein the active agent formulation further comprises a non-ionic surfactant.

7. The osmotic dispenser as defined by claim 6, wherein the surfactant is selected from the group consisting of sorbitan mono-stearate, polyoxyethylene (20) sorbitan monooleate, and polyoxyethylene 40 stearate.

8. The osmotic dispenser as defined by claim 1, wherein the active agent formulation further comprises an anti-oxidant.

9. The osmotic dispenser as defined by claim 8, wherein the anti-oxidant is selected from the group consisting of 2,6-ditertiary-butyl-p-cresol, propyl gallate, tertiary butyl-4-methoxyphenol, ethoxyquin and nordihydroguaiaretic acid.

10. The osmotic dispenser as defined by claim 1, wherein the active agent formulation further comprises an inert particulate solid filler.

11. The osmotic dispenser as defined by claim 6, wherein the active agent is tetracycline and the non-ionic surfactant is sorbitan mono-stearate.

12. The osmotic dispenser as defined by claim 6, wherein the active agent is chloramphenicol and the non-ionic surfactant is polyoxyethylene (20) sorbitan monooleate.

* * * * *